United States Patent
Maness

Patent Number: 6,003,515
Date of Patent: Dec. 21, 1999

[54] MOLDABLE LIP GUARD AND METHOD OF MOLDING SUCH LIP GUARD

[76] Inventor: Bernadette Maness, 1428 Lawn, Angleton, Tex. 77515

[21] Appl. No.: 09/048,972

[22] Filed: Mar. 26, 1998

[51] Int. Cl.⁶ .................................................... A61F 11/00
[52] U.S. Cl. ............................................. 128/857; 128/859
[58] Field of Search ................................... 128/846, 848, 128/859–862; 2/9, 174, 424, 425; 602/74

[56] References Cited

U.S. PATENT DOCUMENTS

| | | | |
|---|---|---|---|
| 2,259,160 | 10/1941 | Glasser | 128/859 |
| 3,103,052 | 9/1963 | Rector | 27/21 |
| 3,126,550 | 3/1964 | Price | 2/174 |
| 3,346,875 | 10/1967 | Weisberger | 128/857 |
| 4,711,237 | 12/1987 | Kaiser | 128/136 |
| 4,949,731 | 8/1990 | Harding | 128/842 |
| 5,152,300 | 10/1992 | Horst | 128/857 |
| 5,447,168 | 9/1995 | Bancroft | 128/859 |
| 5,533,523 | 7/1996 | Bass, Jr. et al. | 128/859 |
| 5,717,993 | 2/1998 | Roberts | 128/857 |

*Primary Examiner*—Michael A. Brown
*Attorney, Agent, or Firm*—Joseph N. Breaux

[57] ABSTRACT

A moldable lip guard for musicians with orthodontic appliances, such as, without limitation, braces, wherein a posterior surface of the moldable lip guard is mold to and imprinted with the anatomic profile of the upper or lower front teeth with overlaid orthodontic appliance. The molded and imprinted posterior surface when coupled to the upper or lower front teeth prevents displacement of the moldable lip guard when playing a musical instrument. The curved and smooth anterior surface of the moldable lip guard serves to eliminate the pain and discomfort associated with embouchure and playing of various types of musical instruments and, especially, brass instruments. The thin thickness of the moldable lip guard does not hinder the musician's ability to project a forceful stream of air through the lips to the instruments mouthpiece when playing such instrument.

1 Claim, 2 Drawing Sheets

MOLDABLE LIP GUARD AND METHOD OF MOLDING SUCH LIP GUARD

TECHNICAL FIELD

The present invention relates to protective mouthpieces and, more particularly, to a moldable lip guard for musicians with orthodontic appliances, such as, without limitation, braces, wherein a posterior surface of the moldable lip guard is mold to and imprinted with the anatomic profile of the upper or lower front teeth with overlaid orthodontic appliance. The molded and imprinted posterior surface when coupled to the upper or lower front teeth prevents displacement of the moldable lip guard when playing a musical instrument. The curved and smooth anterior surface of the moldable lip guard serves to eliminate the pain and discomfort associated with embouchure and playing of various types of musical instruments and, especially, brass instruments. The thin thickness of the moldable lip guard does not hinder the musician's ability to project a forceful stream of air through the lips to the instruments mouthpiece when playing such instrument.

BACKGROUND OF THE INVENTION

Musicians wearing braces experience pain and discomfort and injury to the superior and/or inferior labia mucosa while playing a brass instrument. Brass instruments have mouthpieces (hereinafter sometimes referred to as the "instrument's mouthpiece") which provide an opening for receiving a projected stream of forced air from the musicians mouth. The instrument's mouthpiece abuts the exterior side of the lip and/or mouth/lip area. However, if the musician is wearing braces along the upper and/or lower teeth, the wiring and bracing elements become embedded in the superior and/or inferior labia mucosa causing injury thereto which results in pain and discomfort. While there are protective mouthpieces which are received in the mouth between the teeth and the lips to protect against trauma, such protective mouthpieces are not anatomically designed for musicians to allow the musician's lips to be puckered in a manner suitable for forcing air through the lips to play an instrument.

Several devices have been patented which are aimed at mouthpieces.

U.S. Pat. No. 5,533,523, to Bass, Jr. et al., entitled "MEDICAL MOUTHPIECE" discloses a mouthpiece having two spaced flanges to fit over the outside of the lips on the proximal end of the mouthpiece and behind the front teeth on the distal end of the mouthpiece with the intermediate space to be clamped between the bitting front teeth. A central hollow passageway permits the instrument to be inserted. A lower curved tongue plate extends inwardly and downwardly to depress the patients tongue and to guide the forward end of the instrument.

U.S. Pat. No. 5,447,168, to Bancroft, entitled "MOUTH-GUARD" discloses a mouthguard for protecting lips against impact trauma on orthodontic appliances (braces), protecting teeth from sports trauma, protecting teeth from clashing together or grinding; and protecting the temporomandibular joint (TMJ) from traumas due to a blow to the mandible. The mouthpiece comprises a curved flexible element, having two or more substantially central apertures extending therethrough and a notched portion on the upper and lower surface thereof. On the inner posterior surface of the element, an inwardly projecting portion extends at right angles thereto on each side of the aperture and designed to be grasped by the teeth. The mouthguard lays against the outer surface of the teeth with the curved flexible element and extends into the buccal folds superiorly and interiorly of the cheek where the muscles hold it in place.

U.S. Pat. No. 5,152,300, to Horst, entitled "GUARD FOR PROTECTING THE CORNER OF A PATIENT'S MOUTH" discloses a guard made of soft flexible material and includes a pair of hinged wings adapted to be placed in straddling relation with the cheek of a dental patient. A forwardly facing and generally V-shaped throat is formed in the forward margins of the wings and cradles and cushions a dental instrument to prevent the instrument from causing sores in the corner of the patient's mouth.

U.S. Pat. No. 4,949,731, to Harding, entitled "ORAL PROPHYLACTICS" discloses an elastic and flexible oral prophylactic that conforms to the mouth, including the lips and tongue. The oral prophylactic is made of impermeable or permeable material and is primarily designed to prevent the spread of disease during oral intercourse. The oral prophylactic has a tubular portion which is received in the mouth and a labial portion that fits over the exterior surface of the lips.

U.S. Pat. No. 4,711,237, to Kaiser, entitled "PROTECTIVE SANITARY BARRIER FOR CPR DOLL" discloses a protective barrier which is a sheet of material with an adhesive on one side and having a central opening. The barrier is placed on the CPR doll with the central opening positioned over the mouth area.

U.S. Pat. No. 3,103,052, to Rector, entitled "NATURAL EXPRESSION FORMER" discloses a device intended for use by morticians to restore the expression of the mouth of a corpse. The device includes two cups and a medial connection between them. The curvature of the cup allows the cups to fit closely to the curvature of the teeth and gums without undue bulging outwardly of the cheeks. The anterior surface of the cups has a plurality of spurs some of which are designed to pierce and so engage the orbicularis oris muscle and thereby to retain the lips closed. Other spurs engage primarily the radial musculature and prevent these muscles from sagging, thereby restoring the natural tension and expression to them and to the face as a whole.

While each of the above mouthpieces function as desired, none of them have a moldable lip guard for musicians with orthodontic appliances, such as, without limitation, braces, wherein a posterior surface of the moldable lip guard is mold to and imprinted with the anatomic profile of the upper or lower front teeth with overlaid orthodontic appliance. The molded and imprinted posterior surface when coupled to the upper or lower front teeth prevents displacement of the moldable lip guard when playing a musical instrument. The curved and smooth anterior surface of the moldable lip guard serves to eliminate the pain and discomfort associated with embouchure and playing of various types of musical instruments and, especially, brass instruments. The thin thickness of the moldable lip guard does not hinder the musician's ability to project a forceful stream of air through the lips to the instruments mouthpiece when playing such instrument.

As will be seen more fully below, the present invention is substantially different in structure, methodology and approach from that of the prior mouthpieces.

SUMMARY OF THE INVENTION

The preferred embodiment of the moldable lip guard of the present invention solves the aforementioned problems in a straight forward and simple manner. What is provided is a moldable lip guard for musicians with orthodontic appliances, such as, without limitation, braces, wherein a posterior surface of the moldable lip guard is mold to and imprinted with the anatomic profile of the upper or lower front teeth with overlaid orthodontic appliance. The molded and imprinted posterior surface when coupled to the upper or lower front teeth prevents displacement of the moldable lip guard when playing a musical instrument. The curved and smooth anterior surface of the moldable lip guard serves to eliminate the pain and discomfort associated with embouchure and playing of various types of musical instruments and, especially, brass instruments. The thin thickness of the moldable lip guard does not hinder the musician's ability to project a forceful stream of air through the lips to the instruments mouthpiece when playing such instrument.

The moldable lip guard of the present invention comprising a moldable lip guard blank elliptically shaped wherein said moldable lip guard blank comprises: a smooth anterior surface and an imprintable posterior surface, wherein the moldable lip guard blank is made of resiliently flexible material which is heat softenable for individualized molding and imprinting and wherein the resiliently flexible material does not decompose and does not become significantly sticky when heated; and wherein the moldable lip guard blank is dimensioned to cover only a plurality of front upper teeth or only a plurality of front lower teeth.

A method of molding a moldable lip guard of the present invention comprises the steps of:

a) providing a moldable lip guard blank made of resiliently flexible material which is heat softenable for individualized molding and imprinting wherein the resiliently flexible material does not decompose and does not become significantly sticky when heated wherein the moldable lip guard blank has a posterior surface;

b) heating the moldable lip guard blank in hot water having a predetermined temperature for a predetermined time interval;

c) removing the heated moldable lip guard blank from the hot water;

d) dipping in cooled water the heated moldable lip guard blank to slightly cool the heated moldable lip guard blank;

e) placing immediately the slightly cooled moldable lip guard blank on front upper teeth or front lower teeth;

f) imprinting on said posterior surface an imprint pattern of the front upper teeth and overlaid orthodontic appliances thereon or the front lower teeth and the overlaid orthodontic appliances thereon and molding the slightly cooled moldable lip guard blank to the anatomic curved contour in which the front upper teeth or the front lower teeth define;

g) removing the imprinted and molded lip guard blank; and, h) setting the imprint pattern of the molded and imprinted moldable lip guard blank to form an individualized moldable lip guard.

In view of the above, an object of the present invention is to provide a moldable lip guard which is elliptically shaped blank and made of resiliently flexible material which is heat softenable for individualized molding and imprinting. More specifically, the resiliently flexible material does not decompose or become significantly sticky and stretchy when heated. The molding process heats the moldable lip guard a sufficient amount so as to only soften the resiliently flexible material to allow the posterior surface of the moldable lip guard to be molded to and imprinted with the anatomic profile of the upper or lower front teeth with overlaid orthodontic appliances of the individual. Thereafter, the molding process sets the finalized imprint by cooling the moldable lip guard after having been molded and imprinted.

Another object of the present invention is to provide a moldable lip guard which is highly suited for musicians with orthodontic appliances which play brass instruments such as without limitation, a trumpet, a cornet, a trombone, a french horn, a euphonium, and a tuba. Nevertheless, the moldable lip guard can be worn by a musician playing any instrument which requires the instrument's mouthpiece to abut the lip or mouth area.

A further object of the present invention is to provide a moldable lip guard, especially, suited for musicians wherein the thin thickness of the moldable lip guard provides the necessary buffer to shield the superior and/or inferior labial mucosa from pain and injury when playing a musical instrument without compromising the musicians ability to play the instrument. Thereby, the moldable lip guard in not bulky and is not cumbersome to use or insert in the mouth.

It is a still further object of the present invention to provide a moldable lip guard which has a thickness of approximately 1/16 of an inch; a length of approximately 2 inches and a maximum width of approximately 9/16 of an inch.

It is a still further object of the present invention to provide a pair of moldable lip guards wherein one moldable lip guard of the pair is molded to and imprinted with the anatomic profile of the upper front teeth with overlaid orthodontic appliance thereon and the other moldable lip guard of the pair is molded to and imprinted with the anatomic profile of the lower front teeth with overlaid orthodontic appliance thereon. Thereby, the pair of moldable lip guards provide the necessary protection for a musician having orthodontic appliances overlaid on the upper and lower teeth when playing an instrument.

It is a still further object of the present invention to provide a moldable lip guard which is dimensioned to cover that portion of the front upper teeth and overlaid orthodontic appliances which would be embedded in the superior labia mucosa when the instrument's mouthpiece is placed to the mouth of the musician. Likewise, another moldable lip guard is provided which is dimensioned to cover that portion of the front lower teeth and overlaid orthodontic appliances which would be embedded in the inferior labia mucosa when the instrument's mouthpiece is placed to the mouth of the musician. Therefore, a clear unobstructed passage from the lungs through the oral cavity to the instrument's mouthpiece is maintained so that the musician can project a sufficient stream of forced air to the instrument's mouthpiece.

It is a still further object of the present invention to provide a method of molding a moldable lip guard which includes heating a pre-formed moldable lip guard blank in hot water having a preferred temperature of approximately 200 degrees Fahrenheit for a predetermined time, such as, 30 seconds. The heated blank is removed therefrom and dipped in cooled water for approximately one second and then immediately placed on the front upper or front lower teeth. Then a sufficient amount of pressure is exerted on slightly cooled blank placed on the front upper or front lower teeth to imprint in the posterior surface the front upper or front lower teeth and the overlaid orthodontic appliances and mold the moldable lip guard blank to the anatomic contour of the front upper or lower teeth. The musician should then seat the instrument's mouthpiece on the lips, pucker the lips in the manner required to play the instrument and project a stream of forced air to make sure a sufficient amount of the front upper or lower teeth and overlaid orthodontic appliances are covered to prevent injury or discomfort when playing the instrument. Thereafter, the molded and imprinted blank is cooled in water to set the mold and imprint to form the moldable lip guard.

In view of the above objects, it is a feature of the present invention to provide a moldable lip guard which is simple to use and mold.

Another feature of the present invention is to provide a moldable lip guard which is relatively simple structurally and simple to manufacture.

A further feature of the present invention is to provide a moldable lip guard which is easily cleaned between uses.

It is a still further feature of the present invention to provide a moldable lip guard which is durable.

It is a still further feature of the present invention to provide a moldable lip guard which is made of material which does not have a unpleasant taste when placed within the mouth.

It is a still further feature of the present invention to provide a moldable lip guard which is easily molded to and imprinted with the front upper or lower teeth with orthodontic appliances. Henceforth, the moldable lip guard may be quickly replaced if lost or damaged with a new moldable lip guard.

The above and other objects and features of the present invention will become apparent from the drawings, the description given herein, and the appended claims.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

DESCRIPTION OF THE EXEMPLARY EMBODIMENT

Figure 1:
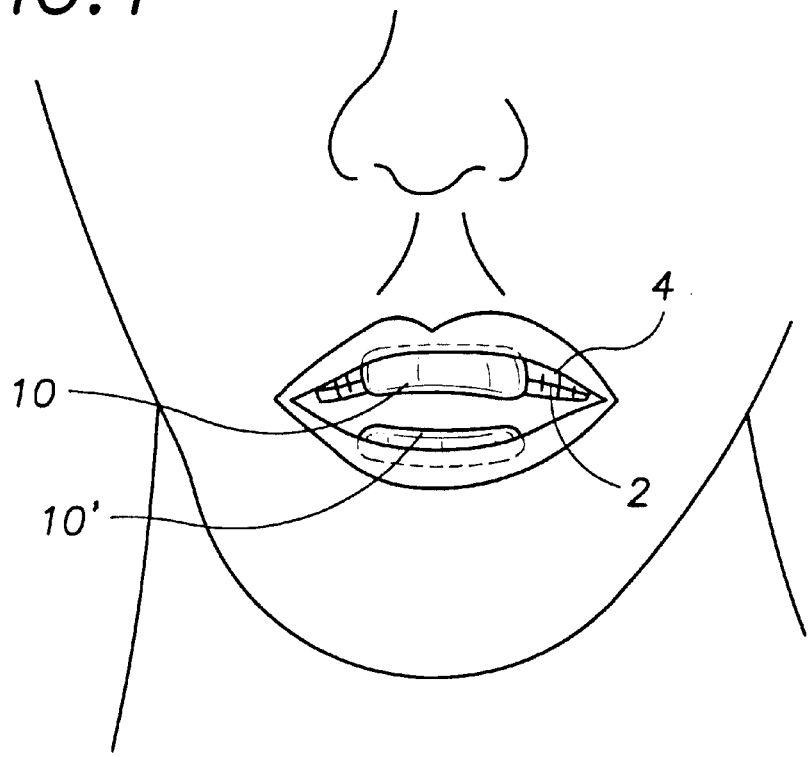
FIG. 1 illustrates a perspective view of the preferred embodiment of a pair of moldable lip guard of the present invention in use.
Figure 3:
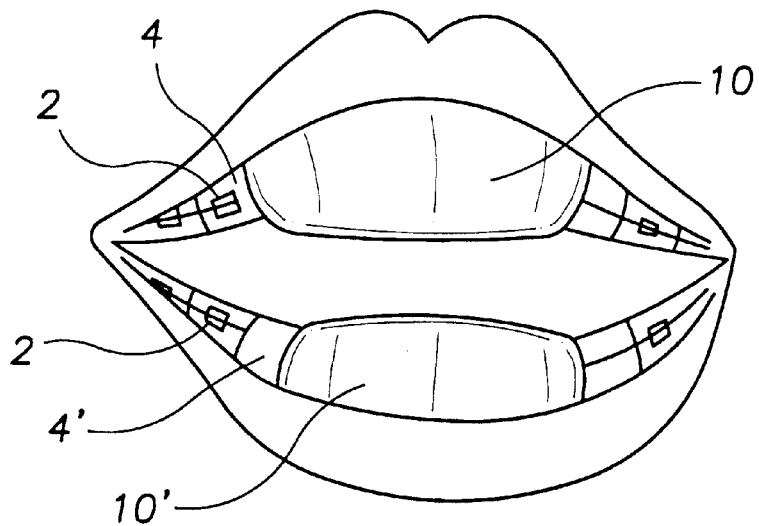
FIG. 3 illustrates a front view of the anterior surface of the moldable lip guard in use; and, FIG. 4 illustrates a side view of the anterior surface of the moldable lip guard in use.
Figure 4:
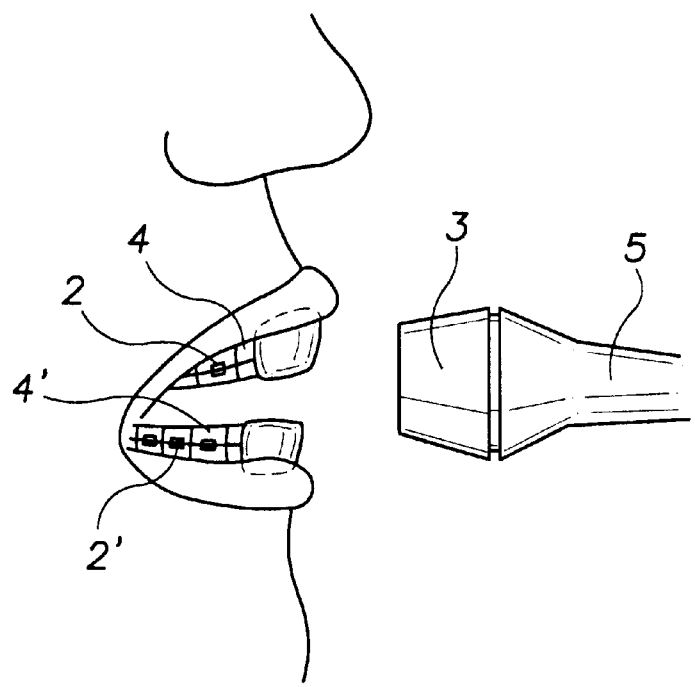

Referring now to the drawings, and in particular FIGS. 1 and 3–4, the moldable lip guard of the present invention is designated generally by the numeral 10 wherein in the exemplary embodiment, a pair of moldable lip guards 10 and 10' are provided to protect the superior and inferior labial mucosa of the wearer when playing instrument 5. Moldable lip guard 10 is comprised of pre-formed moldable lip guard blank 20.

Figure 2A:
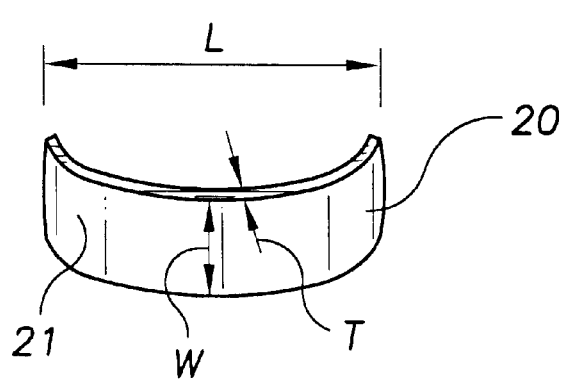
FIG. 2a illustrates a view of the anterior surface of the pre-formed moldable lip guard blank.

Referring now to FIG. 2a, moldable lip guard blank 20 is elliptically shaped and slightly curved wherein the anterior surface 21 and the posterior surfaces are essentially smooth. The moldable lip guard blank 20 is made of resiliently flexible material which is heat softenable for individualized molding and imprinting. Furthermore, the resiliently flexible material does not decompose or become significantly sticky and stretchy when heated.

In the preferred embodiment, moldable lip guard blank 20 has a thickness T of approximately 1/16 of an inch; a length L of approximately 2 inches and a maximum width W of approximately 9/16 of an inch. Thereby, the moldable lip guard blank 20 is dimensioned to cover either the front upper teeth 4 or the front lower teeth 4'. More specifically, moldable lip guard 10 is dimensioned to cover that portion of the front upper teeth 4 and overlaid orthodontic appliances 2 which would be embedded in the superior labia mucosa when the instrument's mouthpiece 3 is placed to the mouth of the musician. Likewise, moldable lip guard 10' is dimensioned to cover that portion of the front lower teeth 4' and overlaid orthodontic appliances 2' which would be embedded in the inferior labia mucosa when the instrument's mouthpiece 3 is placed to the mouth of the musician. Henceforth, a clear unobstructed passage from the lungs through the oral cavity to the instrument's mouthpiece 3 is maintained so that the musician can project a sufficient stream of forced air to the instrument's mouthpiece 3.

In the preferred embodiment, a pair of moldable lip guards 10 and 10' are shown. One moldable lip guard blank 20 is molded to and imprinted with the anatomic profile of the upper front teeth 4 with overlaid orthodontic appliances 2 thereon to form moldable lip guard 10 for the upper front teeth 4. The other moldable lip guard blank 20 is molded to and imprinted with the anatomic profile of the lower front teeth 4' with overlaid orthodontic appliances 2' thereon to form moldable lip guard 10' for the lower front teeth 4'. Thereby, the pair of moldable lip guards 10 and 10' provide the necessary protection for a musician having orthodontic appliances 2 and 2' overlaid on the upper and lower teeth 4 and 4' when playing instrument 5.

Figure 2B:
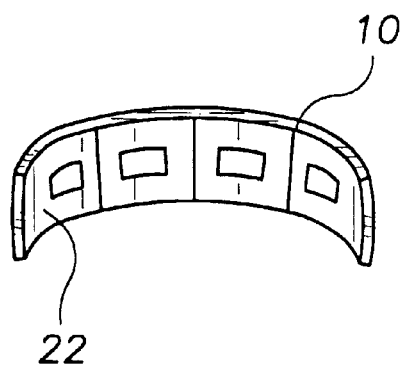
FIG. 2b illustrates a view of the posterior surface of the moldable lip guard having been molded and imprinted with the anatomic profile of the upper or lower front teeth with overlaid orthodontic appliance.

In operation, the (upper) moldable lip guard 10 is positioned over the upper front teeth 4 having overlaid thereon orthodontic appliances 2 wherein when positioning moldable lip guard 10 the imprint pattern on posterior surface 22, as best sen in FIG. 2b, should be aligned with the corresponding upper front teeth 4 having overlaid thereon orthodontic appliances 2 which created such imprint pattern. Likewise, the (lower) moldable lip guard 10' is positioned over the lower front teeth 4' having overlaid thereon orthodontic appliances 2' wherein when positioning moldable lip guard 10' the imprint pattern on posterior surface 22 should be aligned with the corresponding lower front teeth 4' having overlaid thereon orthodontic appliances 2' which created such imprint pattern The imprinted posterior surfaces 22 of the moldable lip guards 10 and 10' when coupled to the upper and lower front teeth 4 or 4', respectively, prevent displacement of the moldable lip guards 10 and 10' when playing musical instrument 5. The curved and smooth anterior surface 21 of the moldable lip guards 10 and 10', as well as, the resilient material in which the moldable lip guards 10 and 10' are made serves to eliminate the pain and discomfort associated with embouchure and playing musical instrument 5 and, especially, brass instruments. The thin thickness of the moldable lip guards 10 and 10' do not hinder the musician's ability to project a forceful stream of air through the lips to the instruments mouthpiece 3 when playing such instrument 5.

In general the moldable lip guard 10 or 10' having such a thin thickness is not bulky and is not cumbersome to use or insert in the mouth. Thereby, moldable lip guard 10 or 10' provides the necessary buffer to shield the superior and/or inferior labial mucosa from pain and injury when playing musical instrument 5 without compromising the wearer's ability to play instrument 5.

The molding process heats the moldable lip guard blank 20 a sufficient amount so as to only soften the resiliently flexible material to allow posterior surface 22 thereof to be molded to and imprinted with the anatomic profile of the upper or lower front teeth 4 or 4' with overlaid orthodontic appliances 2 or 2', respectively, of the individual. Thereafter, the molding process sets the finalized imprint pattern by cooling the moldable lip guard 10 after having been molded and imprinted.

More specifically, the method of molding is generally comprised of providing a moldable pre-formed lip guard blank 20 made of is made of resiliently flexible material which is heat softenable for individualized molding and imprinting wherein the resiliently flexible material does not decompose or become significantly sticky when heated; heating the pre-formed moldable lip guard blank 20 in hot water having a predetermined temperature for a predetermined time interval; removing the heated moldable pre-formed lip guard blank 20 from the hot water; dipping in cooled water the heated moldable pre-formed lip guard blank 20 to slightly cool it. Thereafter, immediately placing the slightly cooled moldable pre-formed lip guard blank 20 on the front upper teeth 4 or the front lower teeth 4' which ever is to be imprinted; exerting a sufficient amount of pressure on the slightly cooled moldable pre-formed lip guard blank 20 placed on the front upper teeth 4 or the front lower teeth 4' to imprint in the posterior surface 22 an imprint pattern of the front upper teeth 41 and the overlaid orthodontic appliances 2 thereon or the front lower teeth 4' and the overlaid orthodontic appliances 2' thereon and mold the curvature of the slightly cooled moldable pre-formed lip guard blank 20 to the anatomic curved contour in which the front upper teeth 4 or front lower teeth 4' define; seating the instrument's mouthpiece 3 on the lips, puckering the lips in the manner required to play the instrument and projecting a stream of forced air to make sure a sufficient amount of the front upper teeth 4 with the overlaid orthodontic appliances 2 thereon or the front lower teeth 4' with the overlaid orthodontic appliances 2' thereon is covered with the imprinted moldable pre-formed lip guard blank 20 such that when playing instrument 5 discomfort is not experienced; removing the imprinted and molded pre-formed lip guard blank 20; thereafter, setting the molded and imprinted moldable pre-formed lip guard blank 20 to form an individualized moldable lip guard. The method is repeated for an additional pre-formed lip guard blank 20 if needed wherein the additional pre-formed lip guard blank 20 is molded and imprinted with an imprint pattern and the anatomic contour of the front upper teeth 4 with the overlaid orthodontic appliances 2 thereon or the front lower teeth 4' with the overlaid orthodontic appliances 2' which ever was not previous imprinted.

The setting step includes placing the molded and imprinted moldable pre-formed lip guard blank 20 in cool water to prevent further molding or imprinting of the molded and imprinted moldable pre-formed lip guard blank 20. Therefore, after the molded and imprinted moldable pre-formed lip guard blank 20 is cooled the resilient flexible material will resiliently flex without distorting or significantly modify the imprint pattern or the molded anatomic curvature of the individualized moldable lip guard.

The preferred predetermined temperature of the hot water is approximately 200 degrees Fahrenheit. The predetermined time interval is approximately 30 seconds. When the heated moldable pre-formed lip guard blank 20 is dipped in cooled water, the heated moldable pre-formed lip guard blank 20 is in such cooled water for approximately one second.

It is noted that the embodiment of the moldable lip guard described herein in detail, for exemplary purposes, is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A moldable lip guard for that portion of the front upper teeth and overlaid orthodontic appliances of a user which would be embedded in the superior labia mucosa (inside upper lip) when the instrument's mouthpiece is placed to the mouth of the musician, said moldable lip guard comprising:

a moldable lip guard blank elliptically shaped wherein said moldable lip guard blank comprises:
a thickness of approximately 1/16 of an inch.
a length of approximately 2 inches,
a maximum width of approximately 9/16 of an inch,
a smooth anterior surface, and
an imprinted posterior surface, wherein the moldable lip guard blank is made of resiliently flexible material which is heat softenable for individualized molding and imprinting and wherein the resiliently flexible material does not decompose and does not become significantly sticky when heated;

wherein the moldable lip guard blank is dimensioned to cover only a plurality of front upper teeth or only a plurality of front lower teeth;

said imprinted posterior surface has imprinted therein an imprint pattern of the plurality of front upper teeth of a user formed therein corresponding to the user's orthodontic appliances wherein said imprint pattern is sized and shaped to secure said posterior surface to said the plurality of front upper teeth having overlaid thereon said orthodontic appliances to prevent the orthodontic appliances from embedding in the superior labia mucosa of a user when the user is playing an instrument positioned against the lips of his mouth.

* * * * *